United States Patent [19]

Smith

[11] Patent Number: 5,034,416
[45] Date of Patent: Jul. 23, 1991

[54] CARBOXYLIC ACID COMPOSITIONS

[76] Inventor: Walton J. Smith, P.O. Box 21, Lebanon, N.H. 03766

[21] Appl. No.: 472,389

[22] Filed: Feb. 1, 1990

Related U.S. Application Data

[63] Continuation of Ser. No. 182,284, Jan. 19, 1988, Pat. No. 4,873,231.

[51] Int. Cl.⁵ .................. A61K 31/19; A61K 31/40; A61K 33/00
[52] U.S. Cl. .................. 514/568; 514/420; 514/569; 514/570; 424/715; 424/717
[58] Field of Search ............... 514/557, 420, 570, 568, 514/569; 424/715, 717

[56] References Cited

U.S. PATENT DOCUMENTS 4,687,662  8/1987  Sehobel ........................ 514/557

Primary Examiner—Frederick E. Waddell
Assistant Examiner—Karin F. Weddington
Attorney, Agent, or Firm—Larson and Taylor

[57] ABSTRACT

A pharmaceutically acceptable composition comprising Diflunisal and Naproxen or its salt in combination with a bicarbonate or carbonate.

5 Claims, No Drawings

CARBOXYLIC ACID COMPOSITIONS

This application is a continuation in part application of U.S. Ser. No. 07/182,284, filed Jan. 19, 1988 now Pat. No. 4,873,231.

This invention relates to improved carboxylic acid compositions and their use. More particularly it is concerned with compositions of carboxylic acids which have some useful biological activity and yet display some toxic effects.

It is an object of the present invention to provide a pharmaceutically acceptable composition comprising a biologically active carboxylic acid compound or its salt and a detoxifier for that compound.

This invention is an outgrowth of two discoveries which I have made relating to biologically active carboxylic acids. The first discovery is that the inherent toxicity of this wide group of compounds is due to the neutralized acid. Previously it had been thought that much or most of the activity of this group of compounds was due to the acid moiety in unneutralized form. Thus, I have discovered that much or most of the biological activity of these compounds is present when neutralized and in salt form.

My second discovery in this connection was that much of the biological activity of salts of carboxylic acids could be made non-effective or neutralized by bicarbonate ions without altering the pH of the carboxylic acid salt.

I have taken advantage of these two major discoveries in developing methods of detoxifying carboxylic acid salts which is the subject of this invention.

So that this invention be better understood, I shall enlarge on these discoveries and further describe this invention.

I have used a variety of test methods to confirm the benefits of this invention. This includes animal studies., however, the basic discovery was made with plants.

DISCOVERY OF THE ACTION OF CARBOXYLIC ACIDS

It should be kept in mind that virtually all tissues are neutral, with slight variations. No matter in what form the carboxylic acid is administered, when it reaches the blood stream, it is in salt form at the same pH as the blood stream.

I have used germinating seedlings for studying the mechanism of a wide variety of water soluble substances. Under very controlled conditions, I can study the various mechanisms in the seedlings by studying the growth with a substance, such as a carboxylic acid salt, and making a comparison with that combining the salt with another substance.

These studies have been going on for several decades under my direction, and we have now completed more than 3,300 separate experiments involving tens of thousands of man hours. The biochemical mechanisms in plants are more readily studied because they are not subject to many of the variables present in animals which often have nothing to do with the subject under investigation. Since plants had to precede animals and humans in the evolution of this planet, it is not surprising that the basic biochemistry is similar and often identical. Animals and humans could not exist without a food source, which plants provided.

Accordingly I have studied many salts of organic acids, and I have demonstrated that the neutralized carboxylic acid group competes with bicarbonate ions.

This competition of carboxylic acid salts with bicarbonate is a natural phenomenon and has been present since the origin of this and probably other planets. It has made possible all forms of life. This process has evolved in a very interesting way, and so that the parameters of this invention may be fully understood, some further description of my discoveries is necessary. This is especially apparent when the great diversity of carboxylic acids is studied.

One of the simplest of carboxylic acids is formic acid, followed by acetic, propionic and butyric acids. I have studied these and dozens of other acids included long chain acids including fatty acids and approaching those acids of the prostaglandin group involved in inflammation. Nature has conveniently made acetic acid (salts) relatively free of anti-bicarbonate activity, and it is not surprising that acetic acid (acetates) make up important building blocks in making more complicated compounds. Most of the other aliphatic acid salts do compete with bicarbonate, and this includes such compounds as salts of Undecylenic acid. Even substituted compounds such as Trimethylacetic acid are strong inhibitors of growth of plantlets, and this inhibition may be reversed with bicarbonate salts.

As stated above, acetates do not seem to interfere with bicarbonate, and many polycarboxylic acids such as citric acid salts, itaconates, glutarates, and many of the compounds of the citric acid cycle do not inhibit growth of plantlets, hence are not interfered with by bicarbonate. I have studied dozens of these compounds and marvel at how evolution as utilized their roles with bicarbonates.

In general, I have found that when there is a substitution alpha to the carboxyl, there is some tendency toward less involvement with bicarbonate ions, and this is especially true when the group alpha to the carboxyl is an amino group. It is therefore not surprising to find that amino acids are relatively non-inhibitory to growth and do not interfere with bicarbonate. Nature has thus used this fact to endow amino acids with major roles in life.

The analgesic, Ibuprofen, is a good example of the effect of an alpha substitution with a methyl group. This compound, 2-(4-isobutylphenyl)-propionic acid, is not quite as much involved with bicarbonate ions as one with a similar structure but with a stright chain propionic acid substituent. On the other hand, in my studies in which I study acute toxicity in small fish (guppies), I find that the toxicity of this compound is considerably reduced in the presence of a bicarbonate salt.

Among the various tests which I have used to study these carboxylic acids besides, germinating seedlings and fish, is the inhibition of yeast fermentation of sugar, as measured by the formation of carbon dioxide gas. I have tested a variety of carboxylic acid salts for their ability to inhibit this process. Many of the compounds generally known as NSAIDs (non-steroidal anti-inflammatory agents) show some degree of inhibition of fermentation. Aspirin (Ca Salt) is slightly inhibitory, but I find that compounds like Ibuprofen, are more potent and have good possibilities as agents to reduce distention when the gas formed is due to fermentation of carbohydrates.

SUMMARY OF PARAMETERS OF THIS INVENTION

It is customary in preparing specifications and claims for pharmaceutical patents to limit the invention to a class of chemical, generally narrow and described by a structural similarity.

The potential number of carboxylic acid compounds useful as pharmaceuticals is almost limitless. I have described a fairly wide group of these compounds, and I have shown that this discovery applies to both aliphatic and aromatic classes. Benzoates inhibit growth of plants and much of the inhibition can be reversed with bicarbonates. The same is true of Cyclohexane carboxylic acid (the corresponding alicyclic compound).

In the aliphatic group of compounds, I have shown that there are some carboxylic acid salts such as amino acids which do not interfere with bicarbonate, hence there would be no obvious benefit from a combination with a bicarbonate compound.

Although I have in general limited my discovery to carboxylic acids, there is a group of compounds which technically are not carboxylic acids, but apparently as a result of their acidic character, do interfere to a degree with bicarbonate ions. This group is exemplified by the sweetner, saccharin, and the analgesic piroxicam.

Although I have limited the description of my invention to carboxylic acid salts, it should be recognized that with an excess of bicarbonate, all of these compounds become salts.

My discovery is that there are hundreds of compounds which have a carboxyl group which interferes to a degree with bicarbonate ion. My invention is a combination of a salt of a carboxylic acid with a bicarbonate salt for the purpose of negating this part of the biochemical action when desired. The invention is not limited to oral dosage forms but could even include agricultural applications.

My discovery is new and my invention is new.

The proportion of bicarbonate to carboxylic acid salt is preferably that of a molar excess, eg. about 1.5 to 2 moles antagonist per mole carboxylate. However, 0.5 to 5 moles may be effective and from 1 to 1.5 particularly so. The proportion should however be such as to be additional to any equivalents of bicarbonate that may be present in the composition for some other purpose.

Some of the examples shown below are to clarify my discovery, and some will illustrate examples of application of the discoveries.

EXAMPLES

Example 1

Yeast Fermentation

A mixture of 2% bakers' yeast in water containing 5% sugar in an incubator at 85° F. developed gas which collected at the top of the tube within an hour.

Example 2

Yeast Fermentation Inhibition

In Example 1, 200 mg. Sodium Benzoate were added per 25 cc solution. At the end of two hours there was no carbon dioxide evolution, and substantially none at the end of 5 hours.

Example 3

Reversal of Yeast Fermentation Inhibition

In Example 2, potassium bicarbonate was added at a level of 100 mg/25ml. There was the same rate of carbon dioxide evolution as in Example 1 showing that the action of Sodium Benzoate had been reversed.

Example 4

Cucumber Seedling Growth

Cucumber seeds were placed on a filter paper in a petri dish to which had been added 5 ml of distilled water. They were incubated at 85° F. for two days. Growth was substantial and abundant in this time.

Example 5

Anti-bicarbonate Action of Benzoate

In Example 4, instead of distilled water alone, 5 ml of a solution of sodium benzoate at a level of 1 mg/ml were used in the petri dish. At the end of the incubation period, growth was very much inferior to those in the control.

Example 6

Reversal of "Antibicarbonate" action

In Example 5, potassium bicarbonate at the level of 1 mg/ml is added to the solution prior to putting it in the petri dish. At the end of the incubation period, groWth of the seedlings was comparable to the control in Example 4.

Example 7

"Antibicarbonate" action in Fish

Three guppies were put in a solution of sodium benzoate at a level of 3 mg/cc (as benzoic acid). At the end of seven hours, all of the three fish were dead.

Example 8

Reversal of Antibicarbonate action

Three guppies, simultaneously with Example 7, were put in the solution identical with that in "7" but with the addition of potassium bicarbonate at a level of 0.5 mg/ml, all the fish were alive at the end of 7 hours

Example 9

"Antibicarbonate" action of Salicylate

In Examples 1 through 8 above, potassium salicylate was substituted for potassium or sodium benzoate, with comparable results.

Example 10

"Antibicarbonate" action of Aspirin

In Examples 4 through 8 above, freeze-dried Calcium Aspirin was substituted for sodium or potassium benzoate with comparable results.

Although it has been indicated above that the action being studied was "antibicarbonate", by way of completeness, it should be stated that although dozens of compounds have no ability to reverse the growth or other inhibition of carboxylate salts, there is some slight reversal of inhibition with substances such as oxalate and citrate which appear to be sources of bicarbonate. The fact that this is not a pH phenomenon is indicated by a lack of reversals with buffer compounds such as Succinates, Pyruvates, Fumarates, and many other members of the citric cycle group.

Example 11

Calcium Aspirin is made by reaction of one molecule equivalent of aspirin with an excess of Calcium Carbonate in water and filtering and freeze-drying. The freeze dried product is combined with one molecular equivalent of sodium bicarbonate. The dose is 5 grains of aspirin.

Example 12

Calcium Aspirin is combined with approximately one equivalent of sodium bicarbonate and formed into a dosage form and enteric coated.

Example 13

Sodium Naproxen is pressed into a tablet with one equivalent of Sodium or Potassium Bi-carbonate to provide a dosage of 200 or 400 mg of Ibuprofen.

Example 14

The dosage form in Example 13 is enteric coated.

Example 15

Guppies were put in a solution containing 0.5 mg/ml of the Sodium salt of Naproxen. They do not live long in this solution, generally about 2 hours. In a parallel experiment, containing the same amount of this compound, guppies added to a similar solution but containing 1 mg/ml of Na Bicarbonate in addition to the Naproxen. lived 12 hours and generally longer.

Example 16

Indomethacin at 0.92 mg/cc was neutralized to form the sodium salt. The solution was divided into two parts, and the one part was combined with sodium bicarbonate at the level of 1 mg/ml. Guppies were added to each of the two solutions. The life expectancy of the guppies was about 2 hours without t he bicarbonate added, and more than doubled with the presence of the bicarbonate.

Example 17

Diflunisal at 0.5 mg/ml was neutralized with sodium hydroxide to a pH of B. and the solution split into two parts, one of which was supplemented with sodium bicarbonate at 1 mg/ml. Guppies were put in each solution. Without the bicarbonate, the life expectancy was about 2 hours, and with the bicarbonate, the guppies lived an average of 19 hours.

Example 18

10 mg of Piroxicam is added to 100 ml of distilled water and using guppies as in Example 17, 100 mg of Sodium Citrate is dissolved. At the end of 12 hours, guppies in a similar solution without the Citrate were dead while those having Sodium Citrate were still alive.

Example 19

In Example 18, Sodium Bicarbonate was used instead of Sodium Citrate with similar results.

Without repeating here all the studies which were described with salicylates on the above and other compounds, it can be seen that the toxicity of a wide variety of carboxylic acids may be ameliorated by combining the substance with a soluble bicarbonate in a dosage form. It can also be seen that a dosage form utilizing the carboxylic acid as a salt, soluble or less soluble, puts less of a burden on the dosage form to neutralize the acid in the intestinal tract wasting some of the bicarbonate present. It can also be seen that the use of enteric coating in a more sophisticated manner helps the dosage form still more.

It may be wise to differentiate the use of bicarbonates and carbonates. This invention requires the presence of a soluble bicarbonate to be effective. Soluble carbonates naturally are useful since they become bicarhonates in the presence of acid, and they are useful in dosage forms to reduce their size and when there is stomach acid to be neutralized as well. This is also true to some extent of insoluble carbonates such as calcium and magnesium carbonates which are useful in reducing the amount of stomach acid that is available to destroy the bicarbonates present, but they are not as useful otherwise in accomplishing this invention in that their bicarbonates are unstable or not existent. Nevertheless, this invention visualizes a degree of usefulness for insoluble carbonates and emphasizes the value of soluble bicarbonates.

We have confirmed that the carbonate may be in several forms and still be useful for accomplishing this invention, and an example of one useful form that represents a combination with another substance are compounds of sodium carbonate with antacids, and this is exemplified by the substance, Dihydroxyaluminum Sodium Carbonate.

This invention may be accomplished by taking a bicarbonate along with the biologically active drug or often just prior or just after taking the drug.

Besides the plant, fish, and animal studies, I have recently been able to add another "dimension" to this discovery concerning the metabolic relationship between bicarbonate and certain carboxylic acids. This is in the area of photosynthesis. I have discovered that certain carboxylic acids, expecially salicylates, are able to enhance the rate of photosynthesis in the algae, Chlorella.

The medium used for these studies was a solution of inorganic compounds satisfactory for growing plants hydroponically (LiquiSoil®, Windowsill Gardens, Lebanon, N.H.) The Chlorella algae grow well in this medium in the presence of carbon dioxide. A standard dilution solution of Liqui-Soil in which chlorella were already growing was used for the following experiment. To 150 ml of this solution were added 100 mg of Sodium Salicylate in a clear jar. This was put in the sunlight in a window along with a control without the salicylate. At the end of three weeks, the growth of chlorella was enormous in the solution containing salicylate, while the control showed very little additional growth. I have studied quite a few of the carboxylic acids for their ability to enhance growth. Potassium Sorbate and Sodium Benzoate showed a similar property. Sodium Motrin at the same level, in general, was inhibitory. Careful analyses during the course of irradiation showed that while the solution containing salicylate gave a characteristic purple color with ferric nitrate at the start, as the irradiation continued, this t-est diminished indicating that the carboxyl group of the acid was being utilized to supply the carbon dioxide to the chlorella for photosynthesis.

Sodium Bicarbonate added to the same solution containing Chlorella did not promote growth but was more or less inhibitory despite its potential ability to supply carbon dioxide for photosynthesis. This very important finding is submitted with the rest of this disclosure to emphasize the fact that bicarbonate is involved in biochemical reactions involving non-steroidal inflammatory agents. This latter discovery has the potential of supplying a method for production of oxygen in space travel inasmuch as I have shown that the sodium salicylate (even Aspirin) enhances the production of oxygen resulting from photosynthesis in algae.

I claim:

1. A pharmaceutically acceptable composition comprising a biologically active carboxylic acid compound selected from the group consisting of Indomethacin, Ibuprofen, Diflunisal and Naproxen or its salt and from one to five molar excess of a bicarbonate or carbonate.

2. A composition according to claim 1 comprising 1.5 to 3 moles of Bicarbonate or carbonate per mole of carboxylic acid or its salt.

3. A enteric-coated composition according to claim 1.

4. A pharmaceutically acceptable composition wherein the acid compound is Diflunisal.

5. A pharmaceutically acceptable composition wherein the acid compound is Naproxen.

* * * * *